United States Patent [19]

Rinehart et al.

[11] Patent Number: 5,149,804

[45] Date of Patent: Sep. 22, 1992

[54] ECTEINASCIDINS 736 AND 722

[75] Inventors: Kenneth Rinehart; Ryuichi Sakai, both of Urbana, Ill.

[73] Assignee: The Board of Trustees of the University of Illinois, Urbana, Ill.

[21] Appl. No.: 620,427

[22] Filed: Nov. 30, 1990

[51] Int. Cl.$^5$ .......................................... C07D 515/22
[52] U.S. Cl. .................................................... 540/466
[58] Field of Search ........................................ 540/466

[56] References Cited

PUBLICATIONS

Rinehart et al., Journal of Natural Products, vol. 53, No. 4, pp. 771-792 Jul. Aug. 1990.
Rinehart et al., Pure & Appl. Chem., vol. 62, No. 7, pp. 1277-1280 (1990).
Wright et al., J. Org. Chem., 55, 4508-4512 (1990).
Rinehart et al., J. Org. Chem., 55, 4512-4515, (1990).
Rinehart et al., Chem. Abstr., 109: 811j (1988).
Ito, CRC Crit. Rev. Anal. Chem., 17: 65-143 (1986).
Nakagawa et al., J. Amer. Chem. Soc., 111: 2721-2722 (1989).
The Merck Index, 11th Edition, page 1540, Monograph No. 9705 (1989).
Lichter et al., Food and drugs from the sea proceedings (1972), Marino Technology society, Washington, D.C. 1973 pp. 117-127.

*Primary Examiner*—Mukund J. Shah
*Assistant Examiner*—Jyothsna Venkat
*Attorney, Agent, or Firm*—Ernest V. Linek

[57] ABSTRACT

Ecteinascidins 722 and 736 (Et's 722 and 736) have been isolated from the Caribbean tunicate *Ecteinascidia turbinata* and their structures have been assigned as tetrahydro-β-carboline-substituted bis(tetrahydroisoquinolines) related to the previously reported Et's 729 and 743. Et's 722 and 736 protect mice in vivo at very low concentrations against P388 lymphoma, B16 melanoma, and Lewis lung carcinoma.

3 Claims, 3 Drawing Sheets

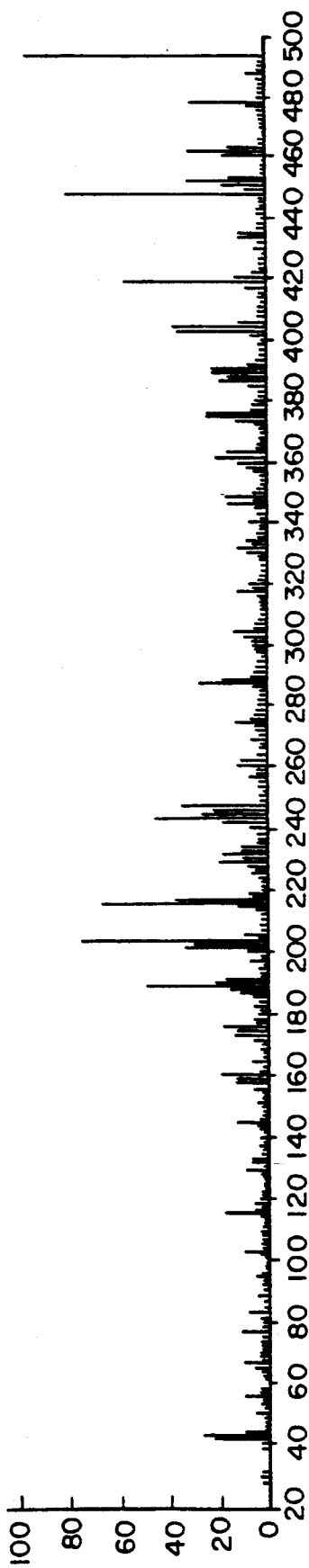
FIG. IA
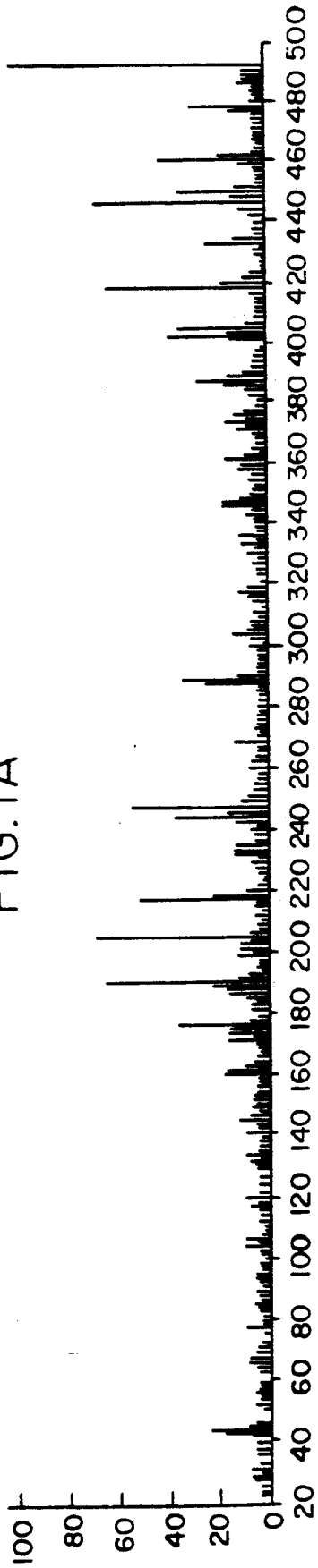
FIG. IB

ECTEINASCIDINS 736 AND 722

STATEMENT OF GOVERNMENT SUPPORT

This invention was supported in part by a grant from the National Institute of Allergy and Infectious Diseases (No. AI04769). Mass spectra were obtained in the Mass Spectrometry Laboratory, School of Chemical Sciences, University of Illinois, and supported in part by a grant from the National Institute of General Medical Sciences (No. GM27029).

CROSS REFERENCE TO RELATED APPLICATION

This application describes compounds related to those described in copending U.S. Pat. Application Ser. No. 07/548.060. filed Jul. 5, 1990, the disclosure of which is incorporated herein by reference.

BACKGROUND OF THE INVENTION

Rinehart et al. have recently reported on ecteinascidins (Et's) 729 (hydrated molecular weight, 747), 743 (761), 745. 759A,B (777). 770, and their derivatives O-methyl-Et 729 and O-methyl-Et 743. See for example, *J. Orz. Chem.*, 1990, 55, 4512-4515; *Topics in Pharmaceutical Sciences* 1989, Amsterdam Medical Press, 1989, pp. 613-626; *J. Nat. Prod.*, 1990, 53, 771-792; *Biological Mass. Spectrometry*, Elsevier 1990, pp. 233-258; and *Pure Appl. Chem.*, 1990, 62, 1277-1280. Two of those compounds (Et 729, 743) have also been described by others. (See for example, Wright et al., *J. Org. Chem.*, 1990, 55, 4508-4512).

The major component, ecteinascidin 743 (Et 743, (Rinehart et al.. *J. Orz. Chem.*, 1990, 55, 4512-4515), and the others were assigned tris(tetrahydroisoquinoline) structures by correlation NMR techniques, as well as by fast atom bombardment (FAB)MS and tandem MS (FABMS/MS). Among these potent antitumor agents, Et 729 showed especially promising activities vs. tumor cells, but only minute quantities of pure sample were obtained. See for example, Rinehart et al., *Topics in Pharmaceutical Sciences* 1989 pp. 613-626, Amsterdam Medical Press B.V., The Netherlands, (1989), Holt et al., *Diss. Abstr. Int. B.* 47, 3771-3772 (1987) and Rinehart et al., U.S. Pat. Appln. Ser. No. 872,189, filed Jun. 9, 1986; PCT Intl. Appln. W087 07,610, filed Dec. 17, 1987; *Chem. Abstr.*, 109, 811j, (1988).

The need for further biological evaluation promoted the development of a more efficient large-scale isolation procedure. During that process, two new biologically active ecteinascidins; Et 736 (754) and Et 722 (740), were isolated from *Ecteinascidia turbinata* samples collected at various locations in the Caribbean.

SUMMARY OF THE INVENTION

The present invention is directed to the isolation of two new compounds, Et 736 and 722 from *E. turbinata*, together with assignment of their structures and biological activities. The data reported herein support our previously proposed biogiogenetic pathway. See, Rinehart et al., *J. Org. Chem., supra.*

Thus, the present invention is directed to the following new compounds 3, 4 and 5. Compound 1 and 2, Et 743 and 729, respectively, are shown for comparison purposes.

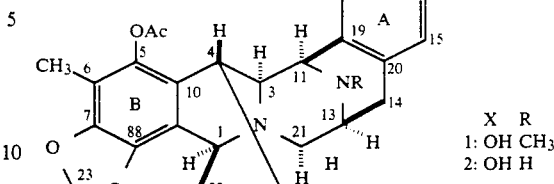

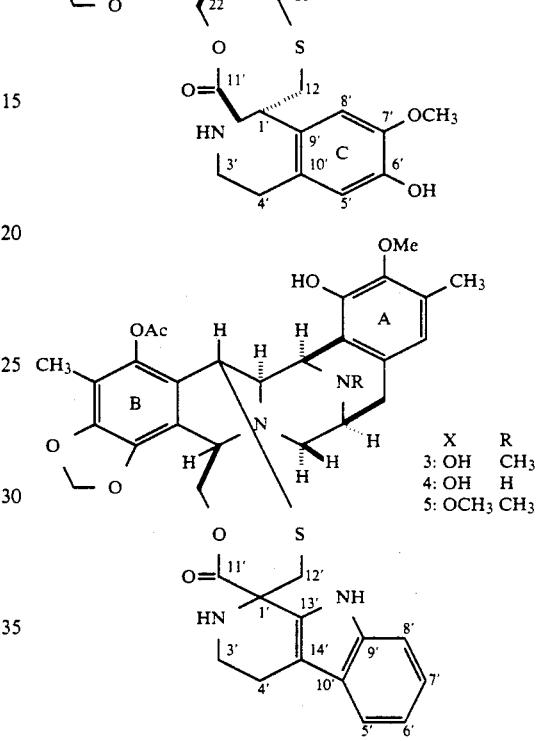

*stereochemistry not determined

BRIEF DESCRIPTION OF THE DRAWINGS

FIG. 1A (top) is the mass spectrum MS/MS (FAB), on a fragment ion at m/z 493 of Et 743.

FIG. 1B (bottom) is the mass spectrum MS/MS (FAB), on a fragment ion at m/z 493 of Et 736.

DETAILED DESCRIPTION OF THE PREFERRED EMBODIMENTS

Figure 2:
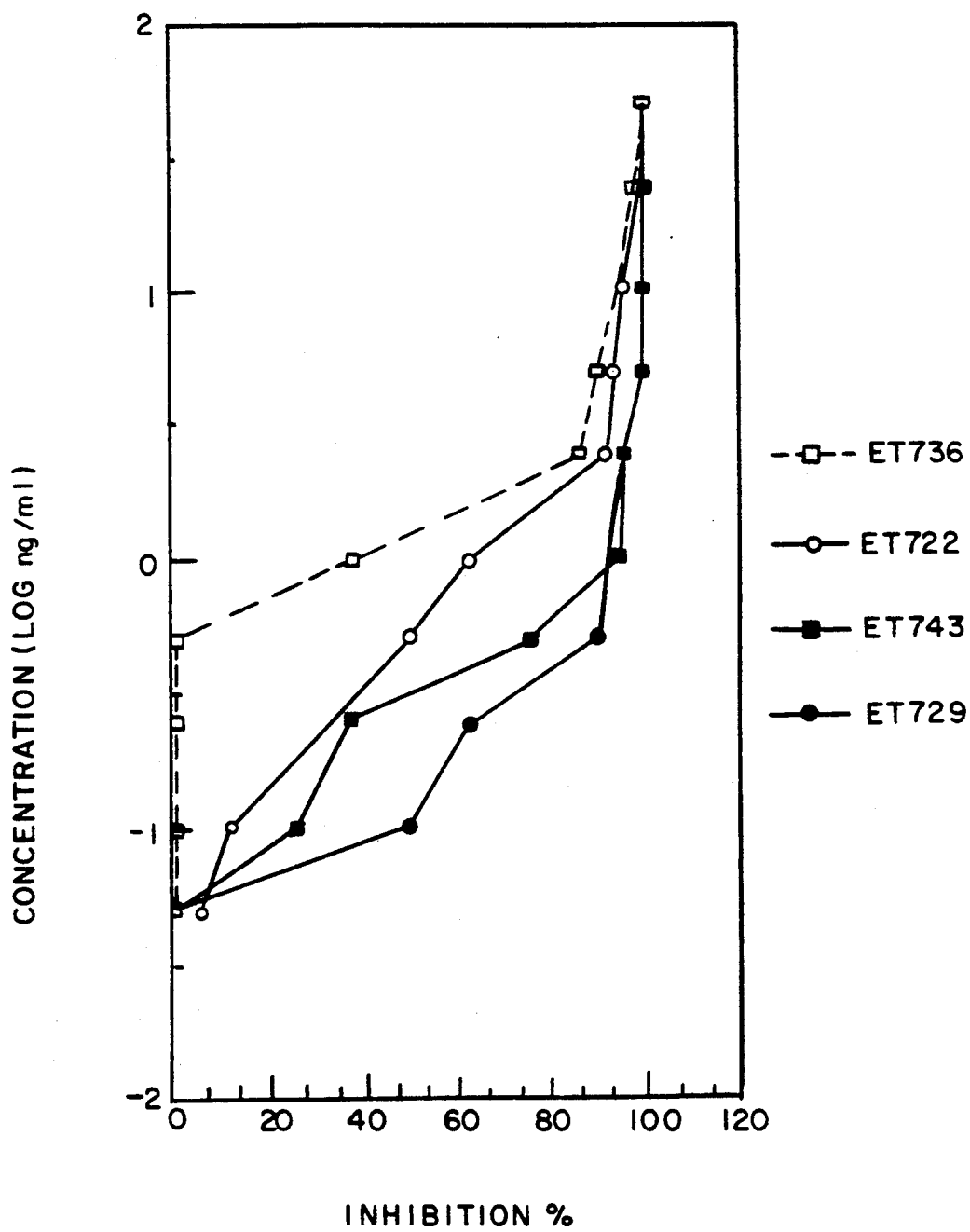
FIGS. 2 and 3 are graphs illustrating the percentage of inhibition of the growth of L1210 cells by Et 736 (- - -) and Et 722 (—). Also shown on the graphs for comparison are the inhibitory effects of Et 743 ( . . .) and Et 729 (—).

Samples of *E. turbinata* were collected in the Florida Keys and Belize, and their cytotoxic extracts were separated by using solvent partition, countercurrent chromatography (CCC), (see for example, Y. Ito, CRC Crit. Rev. Anal. Chem., 17, 65-143, (1986)) and normal and reversed-phase (RP) gravity columns. Final purifications were carried out by (C-18) RP-HPLC.

All samples examined contained Et's 743 (761), 729 (747), 736 (754), and 722 (740) in various proportions. Et 736 (754), $[\alpha]_D = 76°$(c 0.53, CHCl$_3$), showed "molecular" ions at m/z 753.2588 ($C_{40}H_{41}N_4O_9S$, $\Delta 0.6$ mmu, M - H, negative ion HRFABMS). Et 722 (740), $[\alpha]_D = -40°$ (c 1.64, CHCl$_3$), showed "molecular" ions at m/z 739.2433 $C_{39}H_{39}N_4O_8S$, $\Delta$ −0.7 mmu, M +H −H$_2$O, positive ion HRFABMS). $^1$H and $^{13}$C NMR spectra for Et 722 (740) vis-a-vis Et 736 (754) lacked an $N^{12}$—CH$_3$ signal and showed an upfield shift for the adjacent carbons C-11 and C-13 (Table 1), indicating that Et 722 (740) was the $N^{12}$-demethyl derivative of Et 736 (754).

Comparison of NMR data (Table 1) for these new compounds with those for Et 743 (761) and Et 729 (747) indicated that the bis(tetrahydroisoquinoline) units A and B are the same in Et 736 (754) and Et 722 (740) as in the earlier Et's. This was also supported by NMR correlation spectroscopy data, including COSY, phase-sensitive COSY, CSCM, and COLOC sequences, although some of the expected correlations were missing due to the broad peaks observed.

fragmentation patterns. Important fragmentation ions for the A-B bis(tetrahydroisoquinoline) unit observed for Et 743 were also seen for Et 736 (Table II).

TABLE II

Comparison of HRFABMS Fragmentation Data for Et 743 and Et 736

| Observed ions | | | |
|---|---|---|---|
| Et 743 | Et 736 | Formula | Fragment |
| 744.2648 | | $C_{39}H_{42}N_3O_{10}S$ | (M + H − H$_2$O) |
| | 737.2655 | $C_{40}H_{40}N_4O_8S$ | (M + H − H$_2$O) |
| 523.2011 | 523.1960 | $C_{28}H_{31}N_2O_8$ | a + 2H |
| 495.2126 | 495.2126 | $C_{27}H_{31}N_2O_7$ | b + 2H |
| 493.1980 | 493.1980 | $C_{27}H_{29}N_2O_7$ | b |
| 477.1978 | 477.2024 | $C_{27}H_{29}N_2O_6$ | c |
| 463.1837 | 463.1862 | $C_{26}H_{27}N_2O_6$ | d |
| 218.1174 | 218.1180 | $C_{13}H_{16}NO_2$ | g |

TABLE 1

$^1$H and $^{13}$C NME Data for Et's 743, 729, 736, and 722 (1–4) in CD$_3$OD—CDCl$_3$ (3:1)
Chemical shift ($\delta$), multiplicity$^a$ (j in Hz)

| Carbon or Proton$^b$ | 1 | | 2 | | 3 | | 4 | |
|---|---|---|---|---|---|---|---|---|
| | $^{13}$C | $^1$H | $^{13}$C | $^1$H | $^{13}$C$^c$ | $^1$H | $^{13}$C | $^1$H |
| 1 | 56.3, d | 4.78, br s | 56.8, d | 4.69, br s | 54.8, d | 4.71, br s | 56.7, d | 4.72, br s |
| 3 | 58.8, d | 3.72$^e$ | 57.1, d | 3.72 br d (5.5) | 57.8, d | 3.76, br s | 58.5, d | 3.53, d (4.5) |
| 4 | 42.7, d | 4.58, br s | 42.5, d | 4.58, br s | 42.3, d | 4.58, br s | 43.1, d | 4.50, br s |
| 5 | 142.2, s | | 142.3, s | | 140.8, s | | 141.9, s$^d$ | |
| 6 | 113.9, s | | 114.0, s | | 112.6, s | | 113.4, s | |
| 7 | 146.5, s$^d$ | | 146.6, s$^d$ | | 145.4, s | | 146.8, s | |
| 8 | 141.9, s | | 141.5, s | | 140.5, s | | 142.1, s$^d$ | |
| 9 | 116.0, s | | 115.5, s | | 115.4, s | | 115.9, s | |
| 10 | 122.0, s | | 121.4, s | | 120.9, s | | 121.8, s | |
| 11 | 55.6, d | 4.40, br d (3.5) | 47.8, d | 4.73 (5.0) | 54.5, d | 4.73, br s | 48.0, d | 4.44, d (4.8) |
| 13 | 54.0, d | 3.12, br s | 47.2, d | 3.94, d (10.0) | 52.6, d | 3.90, br s | 46.9, d | 3.57, br d (9.0) |
| 14 | 24.5, t | 2.51, 2H, br d (4.5) | 25.1, t | 3.22, d (18.0) 3.12, dd (9.8, 18.0) | 23.2, t | 3.30$^e$ 3.08, dd (10.0, 19.0) | 27.9, t | 3.15, d (17.7) 3.01, dd (17.7, 9.3) |
| 15 | 120.9, d | 6.15, s | 121.2, d | 6.62, s | 120.3, d | 6.70, s | 121.0, d | 6.59, s |
| 16 | 131.2, s | | 130.6, s | | 130.3, s | | 131.4, s | |
| 17 | 145.1, s | | 144.9, s | | 143.0, s | | 144.4, s | |
| 18 | 149.8, s | | 148.6, s | | 148.2, s | | 148.2, s | |
| 19 | 119.2, s | | 120.2, s | | 118.5, s | | 124.3, s | |
| 20 | 131.5, s | | 132.7, s | | 130.9, s | | 132.2, s | |
| 21 | 92.1, d | 4.26, d (3.0) | 90.1, d | 4.33, d (3.0) | 91.5, d | 4.46, d (2.4) | 91.1, d | 4.12, s |
| 22 | 61.2, t | 5.14, d (11.0) 4.09, dd (11.0, 2.0) | 61.5, t | 5.15, d (11.0) 4.11, dd (2.5, 11.0) | 62.0, t | 5.20, dd (12.5, 0.5) 4.18, dd (12.5, 1.5) | 61.6, t | 5.17, d (11.1) 4.14, dd (11.4, 1.2) |
| OCH$_2$O | 103.1, t | 6.07, d (1.0) 5.98, d (1.0) | 103.1, t | 6.09, d (0.5) 6.00, d (0.5) | 101.7, t | 6.26, d (1.0) 6.07, d (1.0) | 103.1, t | 6.21, d (1.0) 6.04, d (1.0) |
| 1' | 65.3, s | | 65.2, s | | 61.9, s | | 63.1, s | |
| 3' | 40.3, t | 3.13, dt (11.0, 4.0) 2.77, ddd (3.5, 5.5, 11.0) | 40.4, t | 3.12, m 2.77, m | 39.6, t | 3.30$^e$ 2.90, dt (11.5, 4.5) | 40.6, t | 3.30, m 2.86, m |
| 4' | 28.6, t | 2.60, ddd (5.5, 10.5, 16.0) 2.42, ddd (3.5, 3.5, 16.0) | 28.6, t | 2.60, ddd (5.5, 10.5, 16.0) 2.42, ddd (3.5, 3.5, 16.0) | 20.9, t | 2.63, m (2H) | 21.6, t | 2.61, m (2H) |
| 5' | 115.6, d | 6.38, s | 115.7, d | 6.39, s | 116.9, d | 7.33, d (8.0 | 118.8, d | 7.31, d (7.8) |
| 6' | 146.4, s$^d$ | | 146.4, s$^d$ | | 117.7, d | 6.92, dt (8.0) | 119.6, d | 6.91, dt (0.9, 7.8) |
| 7' | 146.4, s$^d$ | | 146.4, s$^d$ | | 120.7, d | 7.12, dt (0.6, 8.0) | 122.5, d | 7.00, dt (0.9, 7.8) |
| 8' | 111.3, d | 6.42, br s | 111.3, d | 6.41, br s | 111.7, d | 7.29, d (0.6, 8.0) | 111.9, d | 7.21, d (7.8) |
| 9' | 125.4, s | | 125.2, s | | 126.6, s | | 127.3, s | |
| 10' | 128.8, s | | 129.0, s | | 135.6, s | | 137.4, s | |
| 11' | 173.1, s | | 173.2, s | | 171.2, s | | 172.5, s | |
| 12' | 43.1, t | 2.33, br d (15.5) 2.05$^f$ | 42.7, t | 2.40 2.07$^f$ | 38.9, t | 2.78, d (15.6) 2.15, br d (15.3) | 39.9, t | 2.74, d (15.0) 2.12, br d (15.0) |
| 13' | | | | | 129.3, s | | 130.8, s | |
| 14' | | | | | 109.5, s | | 109.8, s | |
| 5 C=O | 169.8, s | | 169.8, s | | 169.5, s | | 170.7, s | |
| 5 OAc | 20.5, q | 2.29, s | 20.5, q | 2.30, s | 20.3, q | 2.28, s | 20.6, q | 2.27, s |
| 6 CH$_3$ | 9.9, q | 2.01, s | 9.8, q | 2.02, s | 9.4, q | 2.02, s | 9.7, q | 2.01, s |
| 16 CH$_3$ | 16.1, q | 2.28, s | 16.1, q | 2.29, s | 15.7, q | 2.37, s | 16.2, q | 2.32, s |
| 17 OCH$_3$ | 60.2, q | 3.73, s | 60.3, q | 3.71, s | 60.0, q | 3.76, s | 60.3, q | 3.72, s |
| 7' OCH$_3$ | 55.7, q | 3.58, s | 55.6, q | 3.58, s | | | | |
| 12 NCH$_3$ | 41.1, q | 2.23, s | | | 40.9, q | 2.49, br s | | |

$^a$s = singlet, d = doublet, t = triplet, q = quartet, br = broad. $^b$Proton assignments are based on COSY and homonuclear decoupling experiments; carbon multiplicities were determined by APT and DEPT spectra. Carbons for 4 were assigned by analogy to those of 3. $^c$CD$_3$OD—CDCl$_3$, 7:1, $^d$Assignments are interchangeable. $^e$Signals overlap the solvent peak. $^f$Signals overlap the methyl singlet.

Further support for A-B units' identity was provided by HRFABMS (Table II) and FABMS/MS (Scheme I)

TABLE II-continued
Comparison of HRFABMS Fragmentation Data for Et 743 and Et 736

| Observed ions | | Formula | Fragment |
|---|---|---|---|
| Et 743 | Et 736 | | |
| 204.1027 | 204.1025 | $C_{12}H_{14}NO_2$ | h − H |

Scheme I

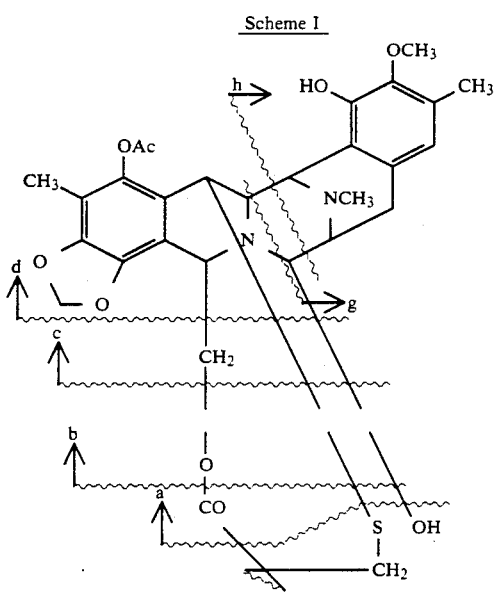

Scheme II

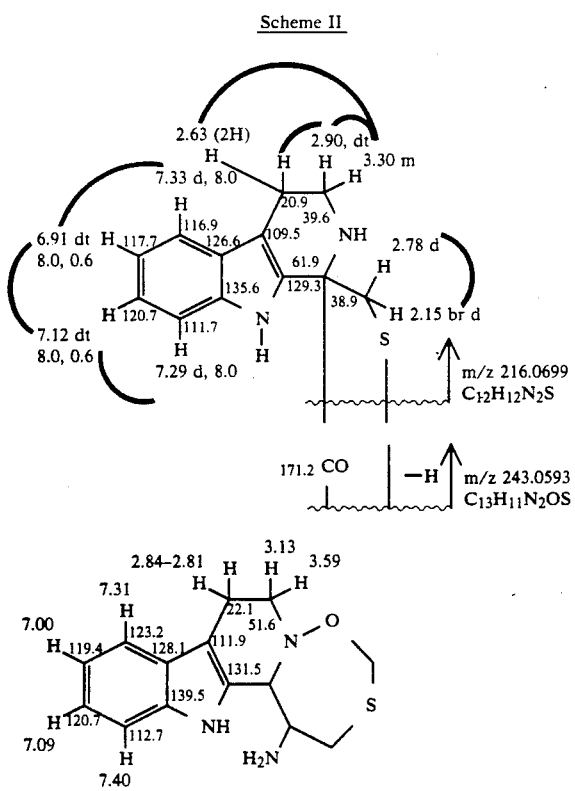

In addition, the tandem FAB mass spectra of the key fragment ion m/z 493 for Et 736 and Et 743 were essentially identical (see FIGS. 1A and 1B), arguing that these Et's contain the same bis(tetrahydro-isoquinoline) subunit.

Addition of 5 μL (ca. 10 equiv.) of methanol-$d_4$ to a $CDCl_3$ solution of Et 736 gave a drastic downfield change in chemical shift for C-21 (δ81 →90) due to the chemical exchange of OH at C-21 by $OCD_3$, just as in the case of Et 743 (67 82 →92), see, Rinehart et al., *J. Org. Chem.*. 1990, 55, 4512–4515. Similarly, treatment of Et 736 with methanol at room temperature and evaporation of the solvent gave O-methyl-Et 736 (754) (5, M − H at 767.2761 for $C_{41}H_{43}N_4O_9S$, Δ0.1 mmu, negative ion HRFABMS), which sh showed a new methoxyl signal (δ53.8, $CDCl_3$) in its hu 13C NMR spectrum.

Subtraction of the bis(tetrahydroisoquinoline) unit (A-B) from the molecular formula for Et 736 (754) gives the formula $C_{13}H_{12}N_2O_2S$ for the rest of the molecule (unit C). The $^{13}C$ NMR signals for this subunit include one carbonyl carbon and eight aromatic/olefinic carbons, leaving three rings for the structure. The UV spectrum (MeOH) $\lambda_{max}$ 292 (ξ11 900), 283 (12 500), 221 (sh 44 800), 207 (11 900) nm along with $^{13}C$ NMR resonances at δ109.5 and 129.3 suggest this structural unit to be a tetrahydro- β-carboline; (see, Shamma et al., *Carbon*-13 NMR Shift Assignments of Amines and Alkaloids: Plenum Press, New York. (1979) and Nakagawa et al., *J. Am. Chem. Soc.*, 111. 2721–2722 (1989) and Rinehart et al., *J. Am. Chem. Soc.*, 23, 3290–3297, (1984)), this was confirmed by COSY spectra showing the aromatic spin system of an ortho-disubstituted benzene ring with signals from δ7.32 to 6.91, as well as an aliphatic $—CH_2—CH_2—X$ spin system (Scheme II). NMR data for unit C closely resemble those of the dihydro-β-carboline debromoeudistomin L. (See, Nakagawa et al., *J. Am. Chem. Soc.*, 111, 2721–2722 (1989). The remaining atoms in unit C —a carbonyl, a $CH_2$, and a sulfur atom - can be assembled as shown in Scheme II to be consistent with the chemical shifts for C-11' and C-12' in Et 743 (see, Table I).

HRMS data on fragmentation ions at m/z 216 and 243, which were seen both in FAB and tandem FAB mass spectra, also supported this assignment (Scheme I). A COLOC spectrum showing a long-range correlation between C-11' and a proton on C-22, along with an IR ($CCl_4$) absorption at 1753 $cm^{-1}$, agreed with an ester linkage between C-11'(carbonyl) and C-22.

The molecular formula $C_{40}H_{42}N_4O_9S$ for Et 736 (754) requires 22 degrees of unsaturation, one more than assigned thus far. The additional ring required is consistent with the $^{13}C$ NMR chemical shifts only if it is formed between the sulfur and C-4 of the isoquinoline B ring, as seen in the Et 743 series. Consequently, the structures of Et 736 and 722 were assigned as 3 and 4. These compounds are closely related biogenetically to those of the Et 743 series, except for their tetrahydro-β-carboline portion, which presumably comes from tryptamine instead of dopamine, (see, Rinehart et al., J. Org. Chem.. 55, 4512–4512, (1990)). Indeed, the water-soluble portion of the same tunicate extract yielded tryptamine itself, also supporting this biogenetic proposal.

Figure 3:
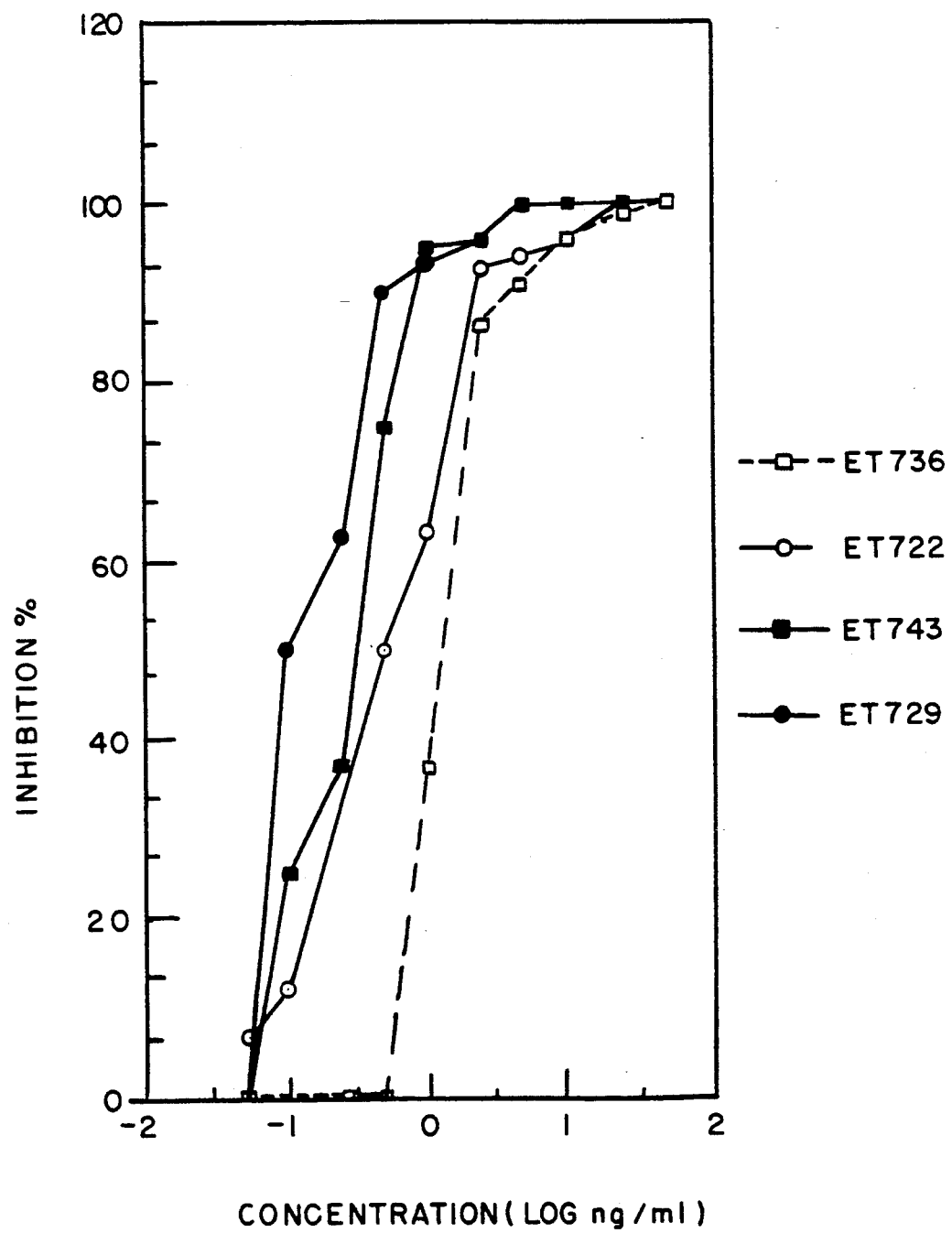

The bioactivities of Et's 722 and 736 appear to be comparable to those of Et's 729 and 743. Et's 722 and 736 inhibit L1210 leukemia cells to the extent of 90% in plate assays at 2.5 and 5.0 ng/mL, respectively (see, FIGS. 2 and 3). More importantly, Et 722 is highly active in vivo, giving T/C 230 (4/6 survivors) at 25 μg/kg day vs. P388 murine leukemia, T/C 200 at 50 μg/kg day vs. B16 melanoma, and T/C 0.27 at 50 μg/kg day vs. Lewis lung carcinoma (see, Table III).

TABLE III

| | Activity in vivo of Ecteinascidins 729 and 722 | | | | | |
|---|---|---|---|---|---|---|
| | P388 lymphocyclic leukemia | | B16 melanoma | | Lewis lung carcinoma | |
| Dose µg/Kg/mi | T/C[a] | Survivors (day) | T/C[a] | Survivors (day) | T/C[b] | Mean tumor volume (ram³) |
| Control | 100 | 0(12) | 100 | 0 | 1.00 | 1512 |
| Et 729 | | | | | | |
| 25.0 | 130 | 0(13) | 76 | 0(42) | 0.00 | 2 |
| 12.5 | 190 | 2(21) | 253 | 5/10(42) | 0.04 | 57 |
| 6.25 | NT | NT | 197 | 0(37) | 0.14 | 216 |
| Et 722 | | | | | | |
| 50.0 | 150 | 1(23) | 200 | 0(36) | 0.27 | 412 |
| 25.0 | >230 | 4(23) | 185 | 0(35) | 0.62 | 934 |
| 12.0 | 205 | 0(23) | 156 | 0(30) | 0.87 | 1319 |

Significant activity: [a]T/C ≥ 125; [b]T/C ≤ 40.

Additional data supporting the activity of Et 722 are shown in the following tables:

TUMOR GROWTH INHIBITION - Day 14

Tumor: 816  
Generation: 77801  
Tissue: SOLID TUMOR  
Level: 1:10 BREI  
Site: 0.5 ml, Sc.  
Species: Mouse  
Strain: 8DF1  
Male  
Source: Charles River Kingston  
DOB:

| Compound | Dose ug/kg/inJ | Schedule & Route | Mean Body Wt Change (grams) Day 1-5 | N.P. D-14 | Median Tumor Vol. (mm 3) | T/C | Mean Tumor Vol. (mm 3) | ST DEV | T/C | T |
|---|---|---|---|---|---|---|---|---|---|---|
| ET 722 | 50.00 | QD1-9, 1P | −0.5 | 0 | 395 | 0.29 | 412* | 157 | 0.27 | 14,862 |
| | 25.00 | | 1.0 | 0 | 908 | 0.66 | 934 | 158 | 0.82 | 7,588 |
| | 12.50 | | 1.9 | 0 | 1204 | 0.88 | 1319 | 509 | 0.87 | 1,420 |

N.P. = # of Non-palpable Tumors on Day 14  
*Significant Activity: T/C < = 0.40 and p = <0.01 By t Test Interim Results: Day 23  
ANTI-TUMOR ACTIVITY VS. P388 LYMPHOCYTIC LEUKEMIA Tumor: 816  
Generation: 77801  
Tissue: SOLID TUMOR  
Level: 1:10 BREI  
Site: 0.5 ml, Sc.  
Species: Mouse  
Strain: 8DF1  
Male  
Source: Charles River Kingston  
DOB:

| Compound | Dose ug/kg/inJ | Schedule & Route | Body Wt. Change (gm) Day 5 | Day of Death | Mean Survival Time | % T/C | Median Survival Time | % T/C | Alive Day 23 |
|---|---|---|---|---|---|---|---|---|---|
| ET 722 | 50.00 | QD1-9, 1P | −0.3 | 10 13 15 15 21 | 14.8 | 145* | 15.0 | 150 | 1 |
| | 25.00 | | 0.2 | 13 21 | | | >23 | >230 | 4 |
| | 12.50 | | 0.4 | 14 19 20 21 22 22 | 19.7 | 199* | 20.5 | 205 | 0 |

N.P. = # of Non-palpable Tumors on Day 14  
*Significant Activity: T/C < = 0.40 and p = <0.01 By t Test Interim Results: Day 42  
ANTI-TUMOR ACTIVITY VS. 816 MELANOMA Tumor: 816  
Generation:  
Tissue: BREI  
Level: 1:10; 0.5 cc  
Species: Mouse  
Strain: 8DF1  
Sex: Male  
Source: Charles River Kingston

| Compound | Dose ug/kg/inJ | Schedule & Route | Change (gm) Day 5 | Day of Death | Survival Time | % T/C | Survival Time | % T/C | Day 24 |
|---|---|---|---|---|---|---|---|---|---|
| ET 722 | 50.00 | QD1-9,1P | −1.1 | 32 32 33 34 34 34 34 35 35 36 | 33.9 | 185* | 34.0 | 200 | 0 |
| | 25.00 | | 0.9 | 28 30 30 30 31 32 34 34 35 35 | 31.9 | 183* | 31.5 | 185 | 0 |
| | 12.50 | | 0.8 | 17 18 23 23 26 27 27 29 30 30 | 25.0 | 144* | 28.5 | 155 | 0 |

816 (0.5 ml, 1:10 brie) implanted ip into male BDF1 mice on day 0, compounds dissolved or suspended in sterile 0.9% NaCl solution (plus minimal amounts of ethanol and Tween-80 as needed) and administered ip days 1-9 in a volume of 0.5 ml/mouse. Mice were weighed days 1 and 5 and deaths were recorded daily.  
*Significant activity: T/C> = 125%

It seems especially promising that some in vivo selectivity is demonstrated by the ecteinascidins; Et 722 is more active than Et 729 vs. P388 (T/C 190 at 12.5 µ/kg day for 729) but less active against B16 (T/C 253 for 729).

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

GENERAL

IR spectra were recorded on an IBM IR/32 FTIR spectrophotometer. Optical rotations were measured with a DIP 370 digital polarimeter with a sodium lamp (589 nm) and 5 cm (1 mL) cell. Melting points were measured with a melting point apparatus and were not corrected. NMR spectra were obtained with QE 300 and GN 500 spectrometers. High- and low-resolution FAB mass spectra and FABMS/MS data were measured on a 70-SE-4F spectrometer. Gravity columns were prepared with silica gel (70-230 mesh) or RP C-18 silica gel (Martex 20-40 $\mu$ or Fuji-Division 100 -200 $\mu$). An Ito multi-layer coil separator-extractor was used for CCC, (Y. Ito, *CRC Crit. Rev. Anal. Chem.*, 17, 65-143, (1986).

EXAMPLE 1

Collection and Extraction. — A sample (19 kg), collected in the Florida Keys in Aug., 1989, and immediately frozen on site, was stored at $-20°$ C. until use. The defrosted sample was squeezed gently by hand, and the solid material was soaked in 2-propanol (4 L $\times$3). The alcoholic extract was separated by decantation from the solid and concentrated to an aqueous emulsion, which was then extracted with $CH_2Cl_2$(0.5 L $\times$8). The $CH_2Cl_2$ extract was concentrated to a crude oil (20.2 g).

EXAMPLE 2

Separation and Purification. — All separations were monitored by bioassays against L1210 murine leukemia cells and *Micrococcus luteus*. The crude extract was partitioned between the lower and upper layers of the solvent system heptane — $CH_2Cl_2$ —$CH_3CN$ (50:15:35). The lower layer was concentrated to an oil (5.76 g), which was partitioned again between the upper and lower layers of the solvent system EtOAc-heptane-MeOH-water (7:4:4:3). The lower layer, showing strong activity, yielded a solid (800 mg), which was partitioned again between the upper and lower layers of the solvent system EtOAc-heptane-MeOH-water (7:4:4:3). The lower layer, showing strong activity, yielded a solid (800 mg), which was then chromatographed to give four fractions over an RP silica gel gravity column with MeOH-aqueous NaCl (0.4 M) (7:1).

The first and most active fraction (333 mg) was separated by CCC into ten fractions with EtOAc-benzene-MeOH-cyclohexane-water (3:4:4:4:3) by using the upper layer as a mobile phase. Fraction 7, containing Et 736 as the major component, was separated by silica gel (treated with $NH_3$) column chromatography with $CHCl_3$-MeOH (12:1). The first fraction (30.4 mg) was purified by C-18 HPLC with $CH_3CN$-MeOH-aqueous NaCl (0.25 M) (5:7:3) to give colorless needles (from $CH_3CN-H_2O$) of 3 (25 mg, 1.3 $\times 10^{-4}\%$): m.p. 140-150° C. dec., IR ($CCl_4$) 3530, 3480 (NH, OH) 2934, 1768 (C=O), 1753 (C=O), 1196, 1153, 1089 cm$^{-1}$; IR (film) 3350, 3200 (NH, OH), 2928, 1753 (C=O), 1440, 1250, 1200, 1088 cm$^{-1}$; [$\alpha$], see above; NMR, see Table I; HRFABMS, see Table II.

Fraction 9 of the CCC separation was chromatographed on a silica gel ($NH_3$ treated) column with $CHCl_3$—MeOH (8:1). The first fraction of this chromatogram was purified by the HPLC system described above to give light-brown solid 4 (4 mg, 2.1 $\times 10^{-5}\%$); m.p. 160-164° C., IR (film) 3291 (NH, OH), 2930, 1753 (C=)), 1440, 1238, 1200, 1086 cm$^{-1}$; [$\alpha$], see above; NMR, see Table I.

Fraction 10 (200 mg), most polar of the CCC separation, was further separated into five fractions by CCC with $CHCL_3$—MeOH—$H_2O$ (4:4:3), using the lower phase as the mobile phase. Fraction 5 (51 5 mg) of this CCC run was separated on a silica gel (50 g) column with $CHCl_3$—MeOH—$H_2O$ (30:20:4) into 11 fractions. Of these, fraction 7 gave crystalline tryptamine hydrochloride (7 mg); m.p. 230° C. dec. (lit, 248° C., see, *Merck Index*, 1989 1540); TLC behavior and spectral data identical with those of an authentic sample (Aldrich).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Ecteinascidin 736, essentially free of cellular material of *E. turbinata*, and having the structural formula:

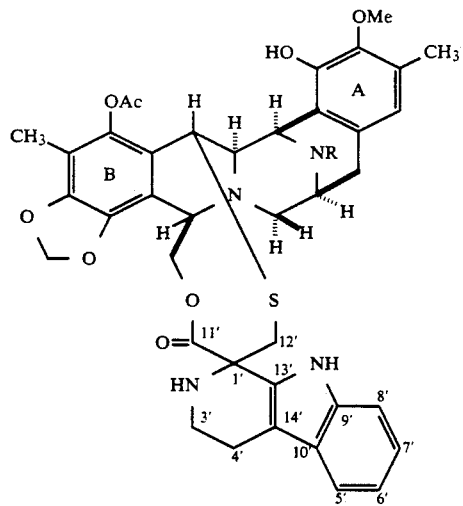

wherein X =OH and R =$CH_3$.

2. Ecteinascidin 722, essentially free of celluar material of *E. turbinata*, and having the structural formula:

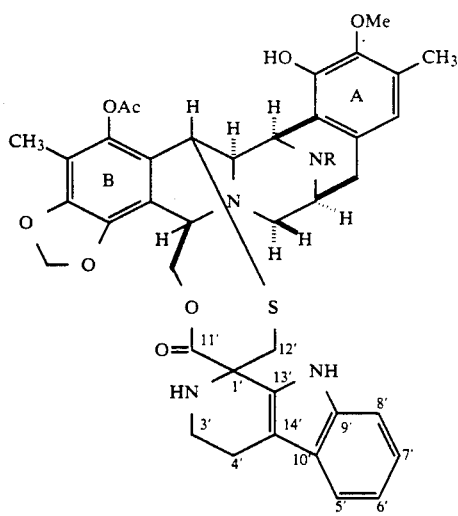
wherein X =OH and R =H.
3. O-Methyl-ecteinascidin 736, essentially free of cellular material of *E. turbinata*, and having the structural formula:
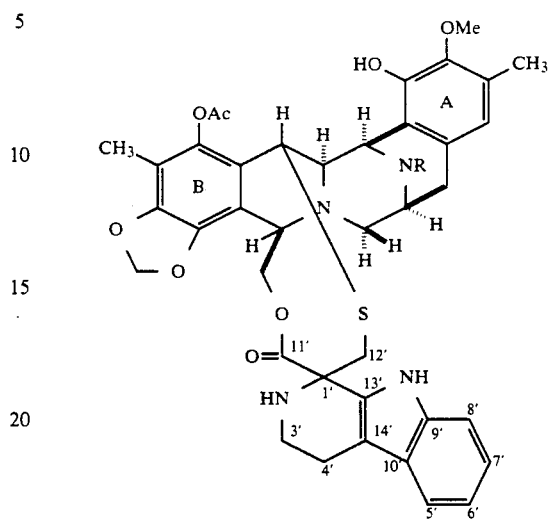
wherein X =OCH₃ and R =CH₃.
* * * * *